US011965960B2

(12) United States Patent
Choi et al.

(10) Patent No.: US 11,965,960 B2
(45) Date of Patent: Apr. 23, 2024

(54) ULTRASOUND IMAGING APPARATUS AND CONTROL METHOD THEREOF

(71) Applicant: SAMSUNG MEDISON CO., LTD., Gangwon-do (KR)

(72) Inventors: Woohyuk Choi, Seoul (KR); Yujin Lee, Seoul (KR); Jae-Keun Lee, Seoul (KR)

(73) Assignee: SAMSUNG MEDISON CO. LTD., Gangwon-Do (KR)

( * ) Notice: Subject to any disclaimer, the term of this patent is extended or adjusted under 35 U.S.C. 154(b) by 574 days.

(21) Appl. No.: 17/149,551

(22) Filed: Jan. 14, 2021

(65) Prior Publication Data

US 2021/0223393 A1 Jul. 22, 2021

(30) Foreign Application Priority Data

Jan. 21, 2020 (KR) .................... 10-2020-0007788

(51) Int. Cl.
*G01S 15/89* (2006.01)
*G01S 7/52* (2006.01)

(52) U.S. Cl.
CPC ...... *G01S 15/8988* (2013.01); *G01S 7/52046* (2013.01); *G01S 7/52079* (2013.01); *G01S 7/52085* (2013.01)

(58) Field of Classification Search
CPC ...... G01S 15/00; G01S 15/89; G01S 15/8988; G01S 7/00; G01S 7/52; G01S 7/52046; G01S 7/52079; G01S 7/52085
See application file for complete search history.

(56) References Cited

U.S. PATENT DOCUMENTS 6,287,258 B1 9/2001 Phillips
6,402,694 B1 * 6/2002 Bae ..................... G01S 7/52046
600/453

(Continued)

FOREIGN PATENT DOCUMENTS

JP 2001-326869 A 11/2001
KR 10-0740378 B1 7/2007
(Continued)

OTHER PUBLICATIONS

Search Report issued by the European Patent Office corresponding to EP Application No. 21152710.6 dated Jun. 15, 2021.

(Continued)

*Primary Examiner* — Nguyen Q. Ha
(74) *Attorney, Agent, or Firm* — Morgan, Lewis & Bockius LLP

(57) ABSTRACT

The ultrasound imaging apparatus provided to quantify the degree of flash artifacts based on an ultrasound echo signal, and to notify a user of an image section with a severe flash artifact includes: a probe configured to irradiate an ultrasound signal to an object and receive an ultrasound echo signal reflected from the object; an image processor configured to obtain a color Doppler signal from which a clutter signal has been completely or partially removed by filtering the ultrasound echo signal, obtain a plurality of consecutive Doppler image frames based on the color Doppler signal and generate a Doppler image based on the plurality of consecutive Doppler image frames; a display configured to output the Doppler image; and a controller configured to calculate a flash artifact score of each of the plurality of consecutive Doppler image frames based on the ultrasound echo signal, generate timeline corresponding to the plurality of consecutive Doppler image frames and control the display so that the (Continued)

flash artifact score of each of the plurality of consecutive Doppler image frames appear on the timeline.

20 Claims, 14 Drawing Sheets

(56) References Cited

U.S. PATENT DOCUMENTS

| | | | |
|---|---|---|---|
| 6,688,177 B2 * | 2/2004 | Wiesauer | G01S 7/52046 73/620 |
| 10,002,427 B2 | 6/2018 | Linard et al. | |
| 10,249,069 B1 | 4/2019 | Kerzner et al. | |
| 2005/0131293 A1 | 6/2005 | Kato | |
| 2015/0320395 A1 | 11/2015 | Sato | |
| 2015/0379700 A1 | 12/2015 | Kamiyama et al. | |
| 2019/0257944 A1 | 8/2019 | Lee et al. | |

FOREIGN PATENT DOCUMENTS

| | | | |
|---|---|---|---|
| KR | 10-1071015 B1 | 10/2011 | |
| KR | 10-2018-0038241 A | 4/2018 | |

OTHER PUBLICATIONS

European Communicationn dated Jul. 26, 2022 issued in European Patent Application No. 21152710.6.
Office Action issued Dec. 7, 2023 for European Patent Application No. 21152710.6.

* cited by examiner

ULTRASOUND IMAGING APPARATUS AND CONTROL METHOD THEREOF

CROSS-REFERENCE TO RELATED APPLICATION

This application is based on and claims priority under 35 U.S.C. § 119 to Korean Patent Application No. 2020-0007788, filed on Jan. 21, 2020 in the Korean Intellectual Property Office, the disclosure of which is incorporated herein by reference.

BACKGROUND

1. Field

The present disclosure relates to an ultrasound imaging apparatus capable of notifying a user of an image meaningful for diagnosis when generating a color Doppler image and a control method thereof.

2. Description of the Related Art

Ultrasound imaging apparatuses operate to irradiate an ultrasound signal generated from an ultrasound probe transducer to a target site inside an object through the surface of the object and receive an ultrasound signal (ultrasound echo signal) reflected from the object to acquire an image of the internal state of the object.

The ultrasound imaging apparatus has advantages in that it is compact and inexpensive, is displayable in real time, and has high safety compared to X-ray diagnostic devices due to having no risk of exposure to X-rays or the like, and thus are widely used in a variety of fields, such as medical fields and the like.

When an object is scanned by selecting the color Doppler mode among the image modes of the ultrasound imaging apparatus, the frequency range of the clutter signal included in the ultrasound echo signal is widened according to various causes.

When the frequency range of the clutter signal is wide, the filter cannot sufficiently remove these signals. When the clutter signal is not sufficiently removed, there is a problem that the unremoved clutter signal remains as a flash artifact in the color Doppler image.

Recently, various algorithms have been developed to efficiently remove the clutter signal, and studies are underway to minimize flash artifacts, but there is no way to prevent the loss of blood flow signals that occurs as the clutter signal is removed.

SUMMARY

Therefore, it is an object of the disclosure to provide an ultrasound imaging apparatus and a control method thereof are provided to quantify the degree of flash artifacts based on an ultrasound echo signal, and to notify a user of an image section with a severe flash artifact.

Therefore, it is an aspect of the disclosure to provide an ultrasound imaging apparatus including: a probe configured to irradiate an ultrasound signal to an object and receive an ultrasound echo signal reflected from the object; an image processor configured to obtain a color Doppler signal from which a clutter signal has been completely or partially removed by filtering the ultrasound echo signal, obtain a plurality of consecutive Doppler image frames based on the color Doppler signal and generate a Doppler image based on the plurality of consecutive Doppler image frames; a display configured to output the Doppler image; and a controller configured to calculate a flash artifact score of each of the plurality of consecutive Doppler image frames based on the ultrasound echo signal, generate a timeline corresponding to the plurality of consecutive Doppler image frames and control the display so that the flash artifact score of each of the plurality of consecutive Doppler image frames appear on the timeline.

The controller may be configured to determine a set of Doppler image frames whose flash artifact score is less than or equal to a preset threshold and which are continuous with each other, among the plurality of consecutive Doppler image frames as a recommended image frame group and control the display so that a section corresponding to the recommended image frame group is displayed on the timeline to be distinguished from a section not corresponding to the recommended image frame group.

The preset threshold may mean one or more thresholds that are automatically set using statistical results of the flash artifact score, and may be reset by a user.

The image processor may be configured to generate a recommended Doppler image by synthesizing Doppler image frames included in the recommended image frame group.

The controller may be configured to control the display so that a marker is displayed on a timeline corresponding to the earliest obtained Doppler image frame and the latest obtained Doppler image frame among Doppler image frames included in the recommended image frame group.

The controller may be configured to control the display so that a color or pattern of a timeline corresponding to Doppler image frames included in the recommended image frame group and a timeline corresponding to Doppler image frames not included in the recommended image frame group are displayed differently.

The recommended image frame group may include a first recommended image frame group and a second recommended image frame group, the image processor may be configured to generate a first Doppler image from which Doppler image frames included in the first recommended image frame group are synthesized and a second Doppler image from which Doppler image frames included in the second recommended image frame group are synthesized, respectively, and the controller may be configured to control the display to display the first Doppler image and the second Doppler image, respectively.

The ultrasound imaging apparatus may further include: an input configured to receive a synthesis command for synthesizing the first Doppler image and the second Doppler image from a user, and the image processor may be configured to generate one Doppler image by synthesizing the first Doppler image and the second Doppler image when receiving the synthesis command.

The input may be configured to receive a selection command for selecting a section of the timeline, the image processor may be configured to generate a third Doppler image by synthesizing Doppler image frames corresponding to the section of the selected timeline based on the selection command, and the controller may be configured to control the display to display a warning image warning of the presence of flash artifact in the third Doppler image when there is a Doppler image frame with the flash artifact score greater than the preset threshold among the Doppler image frames corresponding to the section of the selected timeline.

The flash artifact score may be quantitative information of flash artifact in the plurality of Doppler image frames, and the controller may be configured to determine the flash artifact score of each of the plurality of Doppler image frames based on the power, speed and standard deviation of the ultrasound echo signal.

The controller may be configured to determine whether the probe is scanning the object based on the difference between the ultrasound echo signal and the color Doppler signal, and control the display so that a time point at which the probe starts to scan the object is displayed on the timeline.

Therefore, it is an aspect of the disclosure to provide a control method of an ultrasound imaging apparatus, the method includes: irradiating an ultrasound signal to an object and receiving an ultrasound echo signal reflected from the object; obtaining a color Doppler signal from which a clutter signal has been completely or partially removed by filtering the ultrasound echo signal; obtaining a plurality of consecutive Doppler image frames based on the color Doppler signal; generating a Doppler image based on the plurality of consecutive Doppler image frames; outputting the Doppler image; calculating a flash artifact score of each of the plurality of consecutive Doppler image frames based on the ultrasound echo signal; generating a timeline corresponding to the plurality of consecutive Doppler image frames; and displaying the flash artifact score of each of the plurality of consecutive Doppler image frames on the timeline.

The control method may further include: determining a set of Doppler image frames whose flash artifact score is less than or equal to a preset threshold and which are continuous with each other, among the plurality of consecutive Doppler image frames as a recommended image frame group; and displaying a section corresponding to the recommended image frame group on the timeline to be distinguished from a section not corresponding to the recommended image frame group.

The control method may further include: generating a recommended Doppler image by synthesizing Doppler image frames included in the recommended image frame group.

The displaying a section corresponding to the recommended image frame group on the timeline to be distinguished from a section not corresponding to the recommended image frame group may include: displaying a marker on a timeline corresponding to the earliest obtained Doppler image frame and the latest obtained Doppler image frame among Doppler image frames included in the recommended image frame group.

The displaying a section corresponding to the recommended image frame group on the timeline to be distinguished from a section not corresponding to the recommended image frame group may include: displaying a color or pattern of a timeline corresponding to Doppler image frames included in the recommended image frame group and a timeline corresponding to Doppler image frames not included in the recommended image frame group, differently.

The recommended image frame group may include a first recommended image frame group and a second recommended image frame group, and the control method may further include: generating a first Doppler image from which Doppler image frames included in the first recommended image frame group are synthesized and a second Doppler image from which Doppler image frames included in the second recommended image frame group are synthesized, respectively; and displaying the first Doppler image and the second Doppler image, respectively.

The control method may further include: receiving a synthesis command for synthesizing the first Doppler image and the second Doppler image from a user; and generating one Doppler image by synthesizing the first Doppler image and the second Doppler image when receiving the synthesis command.

The control method may further include: receiving a selection command for selecting a section of the timeline; generating a third Doppler image by synthesizing Doppler image frames corresponding to the section of the selected timeline based on the selection command; and displaying a warning image warning of the presence of flash artifact in the third Doppler image by controlling the display when there is a Doppler image frame with the flash artifact score greater than the preset threshold among the Doppler image frames corresponding to the section of the selected timeline.

The flash artifact score may be quantitative information of flash artifact in the plurality of Doppler image frames, and the calculating a flash artifact score of each of the plurality of Doppler image frames based on the ultrasound echo signal may include: determining the flash artifact score of each of the plurality of Doppler image frames based on the power, speed and standard deviation of the ultrasound echo signal.

The control method may further include: determining whether the ultrasound imaging apparatus is scanning the object based on the difference between the ultrasound echo signal and the color Doppler signal; and displaying a time point at which the ultrasound imaging apparatus starts to scan the object on the timeline.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
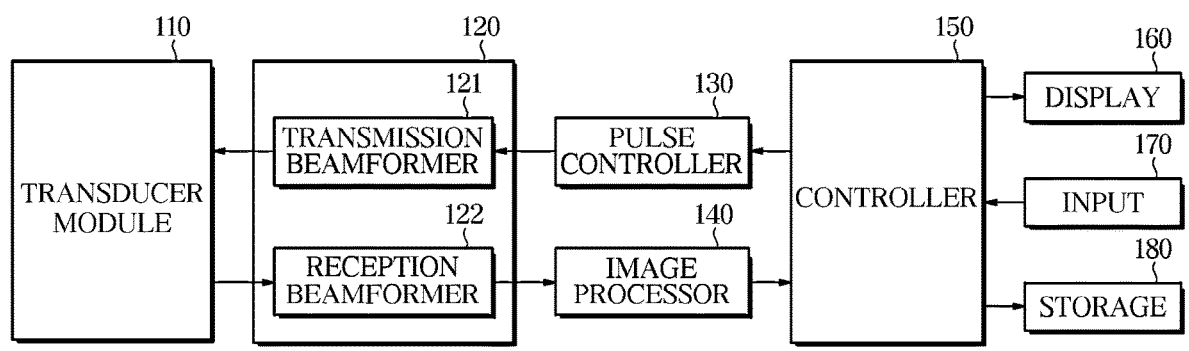
FIG. 1 is a control block diagram of an ultrasound imaging apparatus according to an embodiment.

Like numerals refer to like elements throughout the specification. Not all elements of embodiments of the present disclosure will be described, and description of what are commonly known in the art or what overlap each other in the embodiments will be omitted. The terms as used throughout the specification, such as part", module", member", block", etc., may be implemented in software and/or hardware, and a plurality of parts", modules", members", or blocks" may be implemented in a single element, or a single part", module", member", or block" may include a plurality of elements.

It will be further understood that the term "connect" or its derivatives refer both to direct and indirect connection, and the indirect connection includes a connection over a wireless communication network.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, Further, it will be further understood when a signal or data is transferred, sent or transmitted from "an element" to "another element", it does not exclude another element between the element and the other element passed by the signal or data therethrough, unless the context clearly indicates otherwise.

Although the terms "first," "second," "A," "B," etc. may be used to describe various components, the terms do not limit the corresponding components, but are used only for the purpose of distinguishing one component from another component.

As used herein, the singular forms "a," "an" and "the" are intended to include the plural forms as well, unless the context clearly indicates otherwise.

Reference numerals used for method steps are just used for convenience of explanation, but not to limit an order of the steps. Thus, unless the context clearly dictates otherwise, the written order may be practiced otherwise.

Hereinafter, embodiments of an ultrasound apparatus 100 according to an aspect and a method of controlling the same will be described with reference to the accompanying drawings in detail.

Figure 2:
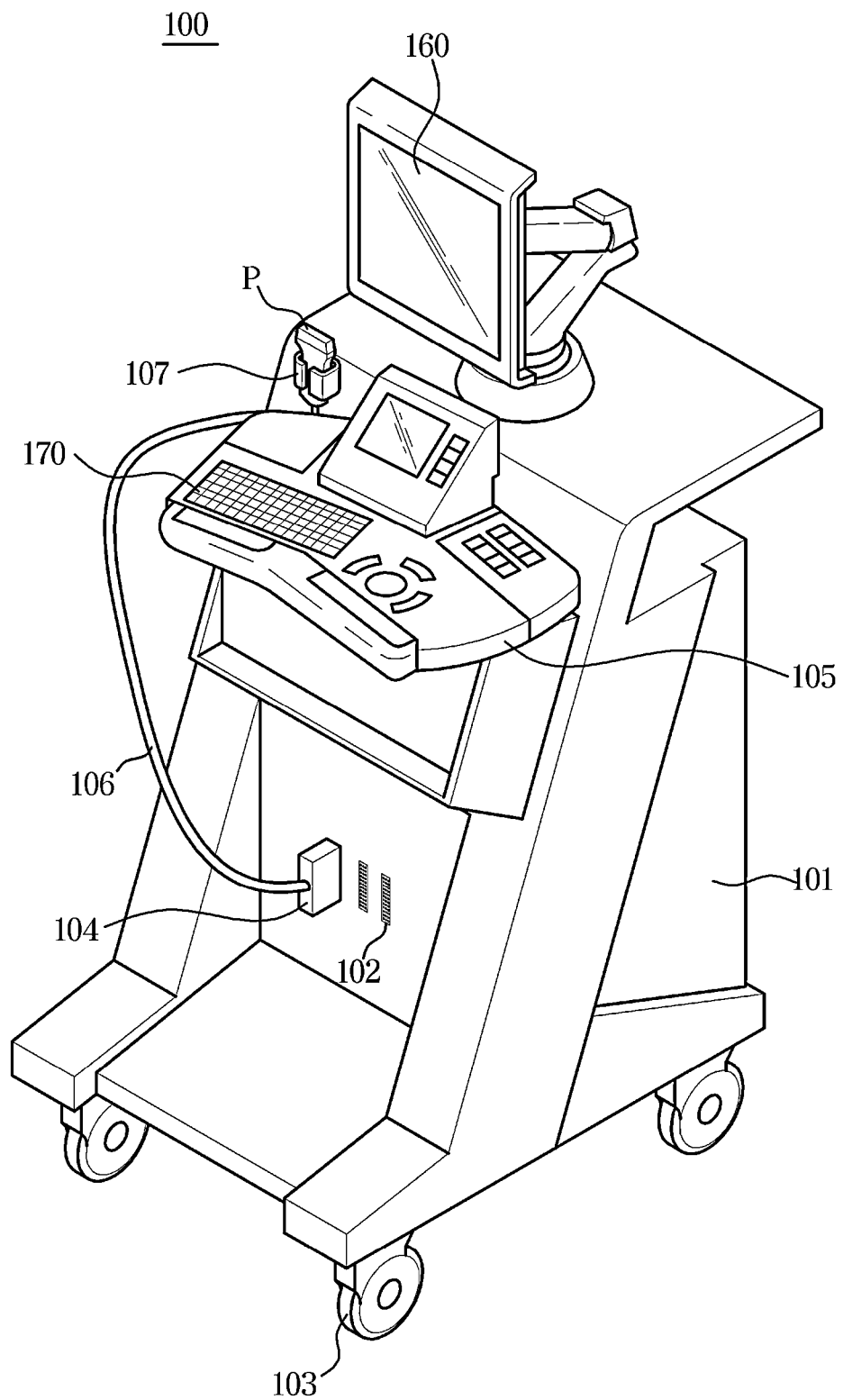
FIG. 2 is an external view of an ultrasound imaging apparatus according to an embodiment.

FIG. 1 is a control block diagram of an ultrasound imaging apparatus according to an embodiment. FIG. 2 is an external view of an ultrasound imaging apparatus according to an embodiment.

Referring to FIGS. 1 and 2 together, the ultrasound imaging apparatus 100 according to an embodiment includes a transducer module 110 that converts an electrical signal and an ultrasound signal to each other, a beamformer 120 that generates a transmission beam and a reception beam, a pulse controller 130 that generates a control signal for generating a pulse and delivers it to the beamformer 120, an image processor 140 that generates an ultrasound image using an echo signal output from the beamformer 120, a controller 150 for controlling the overall operation of the ultrasound imaging apparatus 100, a display 160 for displaying the generated ultrasound image and various data necessary for diagnosis, an input 170 for receiving a users input, and a storage 180 for storing various types of data such as ultrasound image data processed by the image processor 140.

The transducer module 110 may be provided inside the ultrasound probe P, and the ultrasound probe P may be connected to the main body 101 of the ultrasound imaging apparatus 100 through a cable 106.

To this end, one or more female connectors 102 may be provided on the lower front surface of the main body 101. A male connector 104 provided at one end of the cable 106 may be physically coupled to the female connector 102.

The main body 101 is provided at a lower portion with a plurality of casters 103 for the movement of the ultrasound imaging apparatus 100. The user may fix or move the ultrasound imaging apparatus 100 using the plurality of casters 103. Such an ultrasound imaging apparatus 100 is referred to as a cart-type ultrasound imaging apparatus 100.

The main body 101 is provided at a front surface with an operation panel 105. The input 170 for receiving a user's input may be formed on the operation panel 105, and allows a user to input commands for starting a diagnosis, selecting a diagnosis site, selecting a diagnosis type, selecting a mode for ultrasound image, selecting an automatic recommendation function, selecting a timeline 161 section through the input 170. The modes for ultrasound images include A-mode (Amplitude mode), B-mode (Brightness mode), color Doppler mode, D-mode (Doppler mode), E-mode (Elastography mode), M-mode (Motion mode), and the like.

The display 160 may be provided at an upper side of the main body 101. The display 160 may be implemented as at least one of various display panels, such as a liquid crystal display (LCD) panel, a light emitting diode (LED) panel, or an organic light emitting diode (OLED) panel.

In addition, the display 160 may be composed of two or more displays such that each display simultaneously displays a different image. For example, one display may display a 2D ultrasound image, and the other display may display a 3D ultrasound image. Alternatively, one display may display a B-mode image, and the other display may display a color Doppler image.

The display 160 may include a touch screen, and the input 170 may include a touch panel of a touch screen.

One or more probe holders 107 for mounting the ultrasound probe P may be provided on an outer circumferential surface of the main body 101. Accordingly, when the user does not use the ultrasound probe P, the user may store the ultrasound probe P on the probe holder 107.

The probe P may irradiate an ultrasound signal to an object and receive an ultrasound echo signal reflected from the object.

Meanwhile, the beamformer 120 may be provided in the main body 101 or may be provided in the probe P according to an embodiment. In this embodiment, a case where the beamformer 120 is separated from the probe P and provided in the main body 101 is described as an example, but the embodiment of the ultrasound imaging apparatus 100 is not limited thereto.

The main body 101 may include a pulse controller 130, an image processor 140, a controller 150, and a storage 180. The pulse controller 130, the image processor 140, and the controller 150 may include at least one memory in which a program for performing an operation described below is stored and at least one processor for executing the stored program. The pulse controller 130, the image processor 140, and the controller 150 may use separate memories and processors, and may share a memory and a processor.

The storage 180 may include at least one memory for storing ultrasound image data to be described later.

On the other hand, since the appearance of the ultrasound imaging apparatus 100 according to an embodiment is not limited to the example of FIG. 2, the ultrasound imaging apparatus 100 may be implemented as a portable type. When the ultrasound imaging apparatus 100 is implemented as a portable type, the main body may have a shape such as a laptop computer, a PDA, a tablet PC, and the like, and may generate an ultrasound image by connecting an ultrasound probe to the main body.

Figure 3:
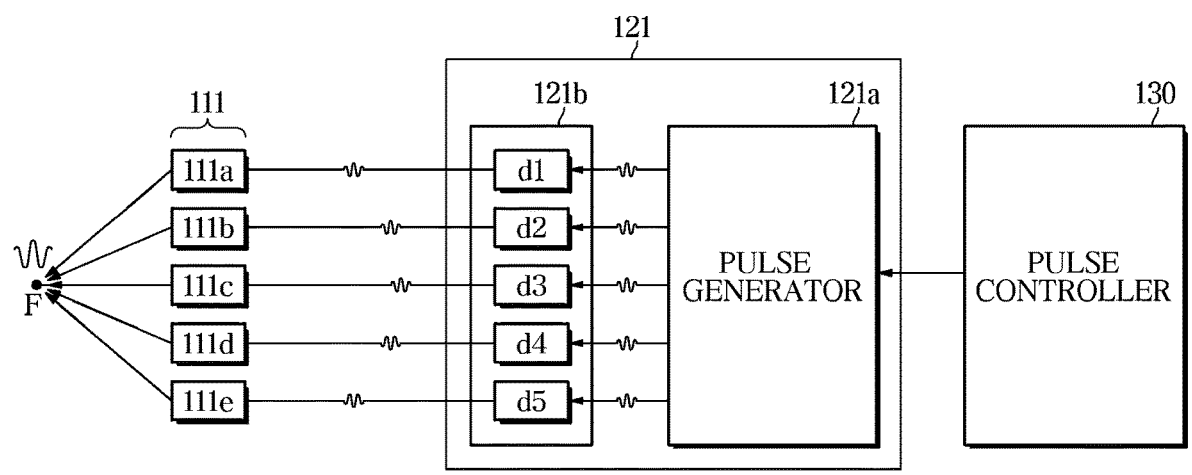
FIG. 3 is a diagram for illustrating an ultrasonic transmission process.
Figure 4:
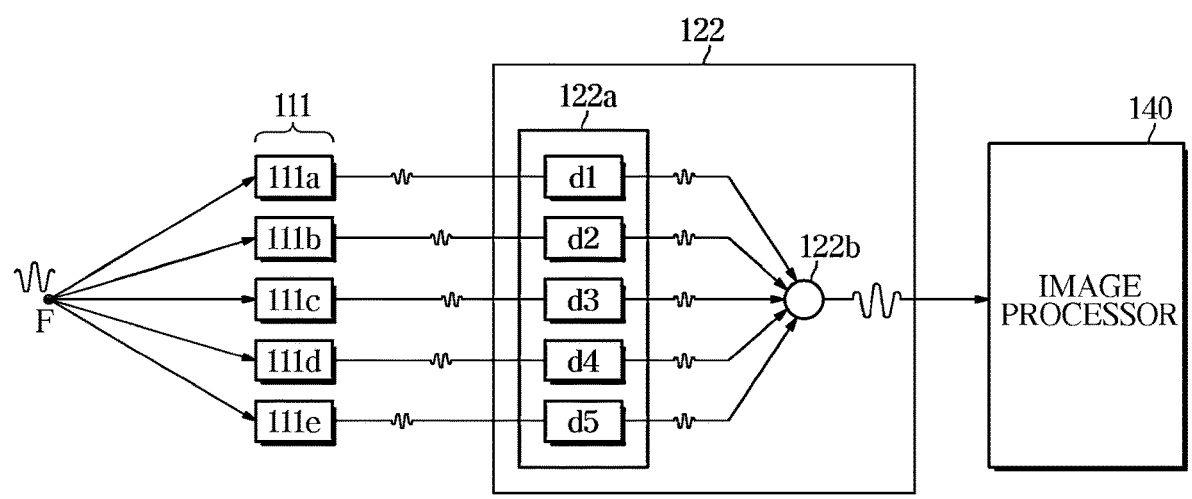
FIG. 4 is a diagram for illustrating an ultrasound reception process.

FIG. 3 is a diagram for illustrating an ultrasonic transmission process. FIG. 4 is a diagram for illustrating an ultrasound reception process.

As illustrated in FIGS. 3 and 4, the transducer module 110 may include a transducer array 111 composed of a plurality of transducer elements, and further includes a switch such as a MUX (multiplexer) for selecting a transducer element to be used for transmission and reception of an ultrasound signal.

For convenience of explanation, in the embodiments to be described later, a case where the transducer array 111 includes five transducer elements 111*a*, 111*b*, 111*c*, 111*d*, and 111*e* will be described as an example.

The transducer element 111 may mutually convert an ultrasonic signal and an electric signal. For example, the transducer element 111 may be implemented as piezoelectric transducers using piezoelectric effects. To this end, the transducer element 111 may include a piezoelectric material or a piezoelectric thin film. When alternating current is applied to the piezoelectric material or piezoelectric thin film from an internal charging device, such as a battery, or an external power supply device, the piezoelectric material or piezoelectric thin film vibrate with a predetermined frequency according to the applied alternating current and ultrasound waves of the predetermined frequency are generated according to the vibration frequency.

On the other hand, when ultrasound echo waves of the predetermined frequency reach the piezoelectric material or piezoelectric thin film, the piezoelectric material or piezoelectric thin film vibrates according to the ultrasound echo waves. In this regard, the piezoelectric material or piezoelectric thin film outputs alternating current of a frequency corresponding to the vibration frequency thereof.

In addition, the transducer element 111 may be implemented as other types of transducer elements, such as a magnetostrictive ultrasonic transducer using the magnetostrictive effect of a magnetic material, or a capacitive micromachining ultrasonic transducer (cMUT) that transmits and receives ultrasonic waves using vibrations of several hundreds or thousands of micromachined thin films.

As illustrated in FIG. 1, the beamformer 120 may include a transmission beamformer 121 and a reception beamformer 122.

The transmission beamformer 121 performs transmission beamforming. As shown in FIG. 3, the distance between the plurality of transducer elements 111*a*, 111*b*, 111*c*, 111*d*, and 111*e* and the focal point F is different. Therefore, the transmission beamformer 121 may generate a transmission beam by applying a time delay so that the ultrasound signal transmitted from each of the transducer elements 111*a*, 111*b*, 111*c*, 111*d*, and 111*e* may simultaneously reach the focal point F on the transmission scan line. When the width of the ultrasound beam is narrowed through the focusing of the ultrasound signal, the lateral direction resolution may be improved.

The transmission beamformer 121 may include a pulse generator 121*a* and a first delay unit 121*b*.

The pulse generator 121*a* generates a pulse according to the control signal of the pulse controller 130. For example, the pulse generated by the pulse generator 121*a* may be a pulse having a pulse repetition frequency (PRF). The pulse generated by the pulse generator 121*a* is input to the first delay unit 121*b*.

The first delay unit 121*b* delays and outputs each pulse output from the pulse generator 121*a* by a predetermined time. The first delay unit 121*b* may include a plurality of delay elements d1 to d5, and the plurality of delay elements d1 to d5 may be connected to the transducer elements 111*a* to 111*e*, respectively.

The delay time of each of the delay elements d1 to d5 is determined according to the distance between the respective transducer elements 111*a* to 111*e* and the focal point F. That is, when the ultrasound signal transmitted from the first transducer element 111*a* and the fifth transducer element 111*e* far from the focal point F reaches the focal point F, the second to fourth delay elements d2 to d4 delay the input pulses for a predetermined time and output them so that the ultrasound transmitted from the second transducer element 111*b* to the fourth transducer element 111*d* reaches the focus F.

As described above, the ultrasound transmitted through the transducer array 111 are reflected on the object and incident on the transducer array 111 again. When the echo ultrasound reflected from the object is received as described above, each of the transducer elements 111*a* to 111*e* outputs an echo signal corresponding to the received echo ultrasound. The echo signal output as described above is input to the reception beamformer 122.

Referring to FIG. 4, the reception beamformer 122 includes a second delay unit 122*a* and a synthesizer 122*b*. Further, although not shown in the drawing, a receiver that receives an echo signal and performs amplification and gain correction may be further included in the reception beamformer 122. When the reception beamformer 122 is implemented as a digital beamformer, it may further include an analog-to-digital converter (ADC) to convert the amplified and gain-corrected analog echo signal into a digital echo signal.

The second delay unit 122*a* may include a plurality of delay elements d1 to d5, and each of the delay elements d1 to d5 may be connected to the transducer elements 111*a* to 111*e*.

Since the times for the echo ultrasound to reach the transducer elements 111*a* to 111*e* are different from each other, the delay elements d1 to d5 delay the input echo signals for a predetermined time in order to focus the echo signals.

For example, the third delay element d3 to which the echo signal is first input delays and outputs the input echo signal until the echo signal is input to the first and fifth delay elements d1 and d5.

The synthesizer 122*b* synthesizes the echo signals output from each of the delay elements d1 to d5. In this case, the synthesizer 212 may synthesize each echo signal by applying a weight.

The image processor 140 generates an ultrasound image based on the echo signal output from the reception beamformer 122. For example, the image processor 140 may generate at least one of an A-mode image, a B-mode image, a D-mode image, an E-mode image, a color Doppler image, and an M-mode image based on the echo signal.

For example, the image processor 140 may obtain a color Doppler signal from which the clutter signal has been completely or partially removed by filtering an ultrasound echo signal to generate a color Doppler image, may obtain a plurality of consecutive Doppler image frames based on a color Doppler signal, and may generate a Doppler image based on the plurality of consecutive Doppler image frames.

In this case, the image processor 140 may generate a Doppler image in which Doppler image frames are consecutively displayed by synthesizing the plurality of consecutive Doppler image frames.

In addition, the image processor 140 may generate a 3D ultrasound image based on a plurality of ultrasound images obtained from the echo signal.

Hereinafter, a method of controlling the ultrasound imaging apparatus 100 including the above-described components will be described in detail.

Figure 5:
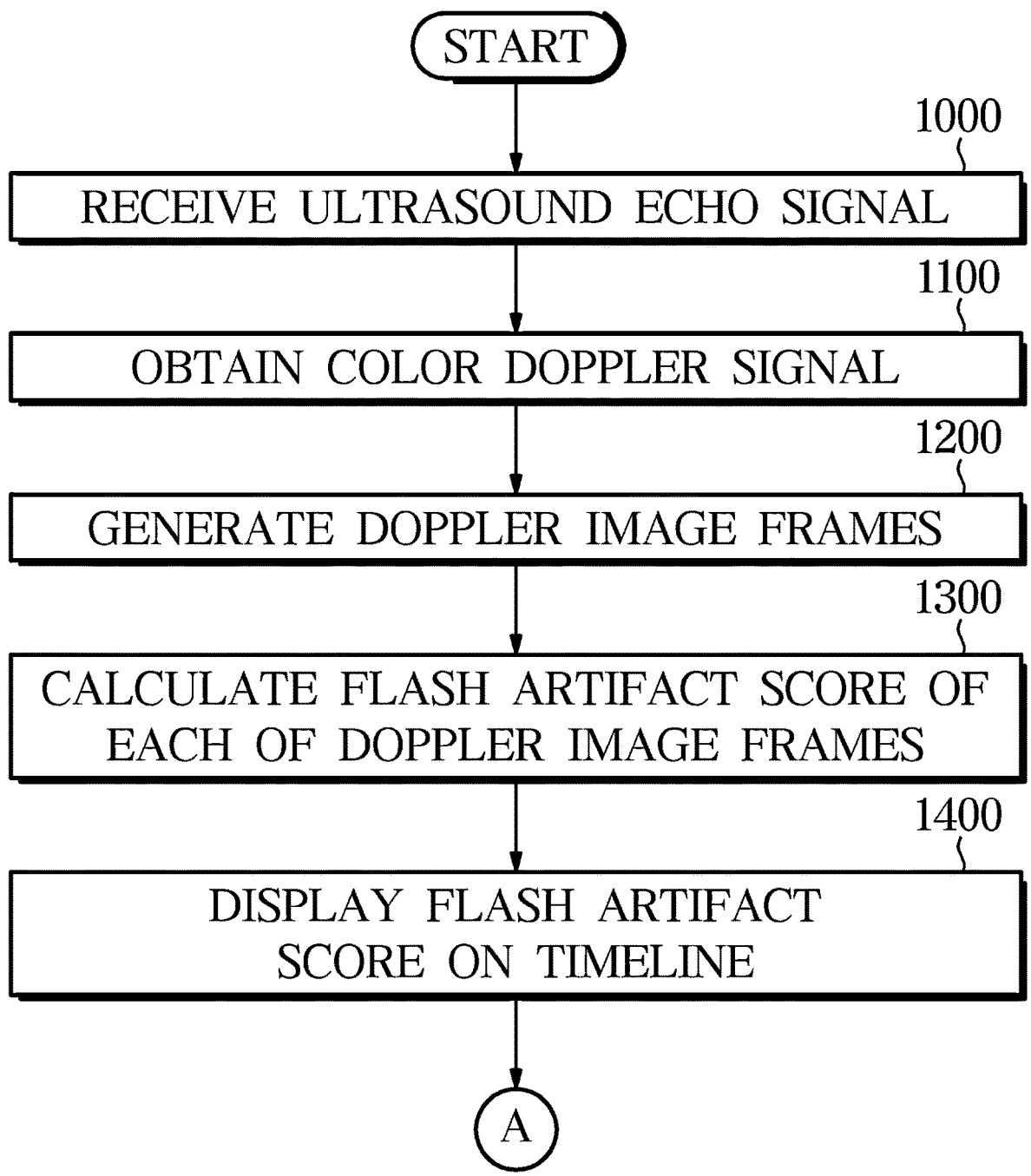
FIGS. 5 to 6 are control flowcharts of an ultrasound imaging apparatus according to an embodiment.
Figure 6:
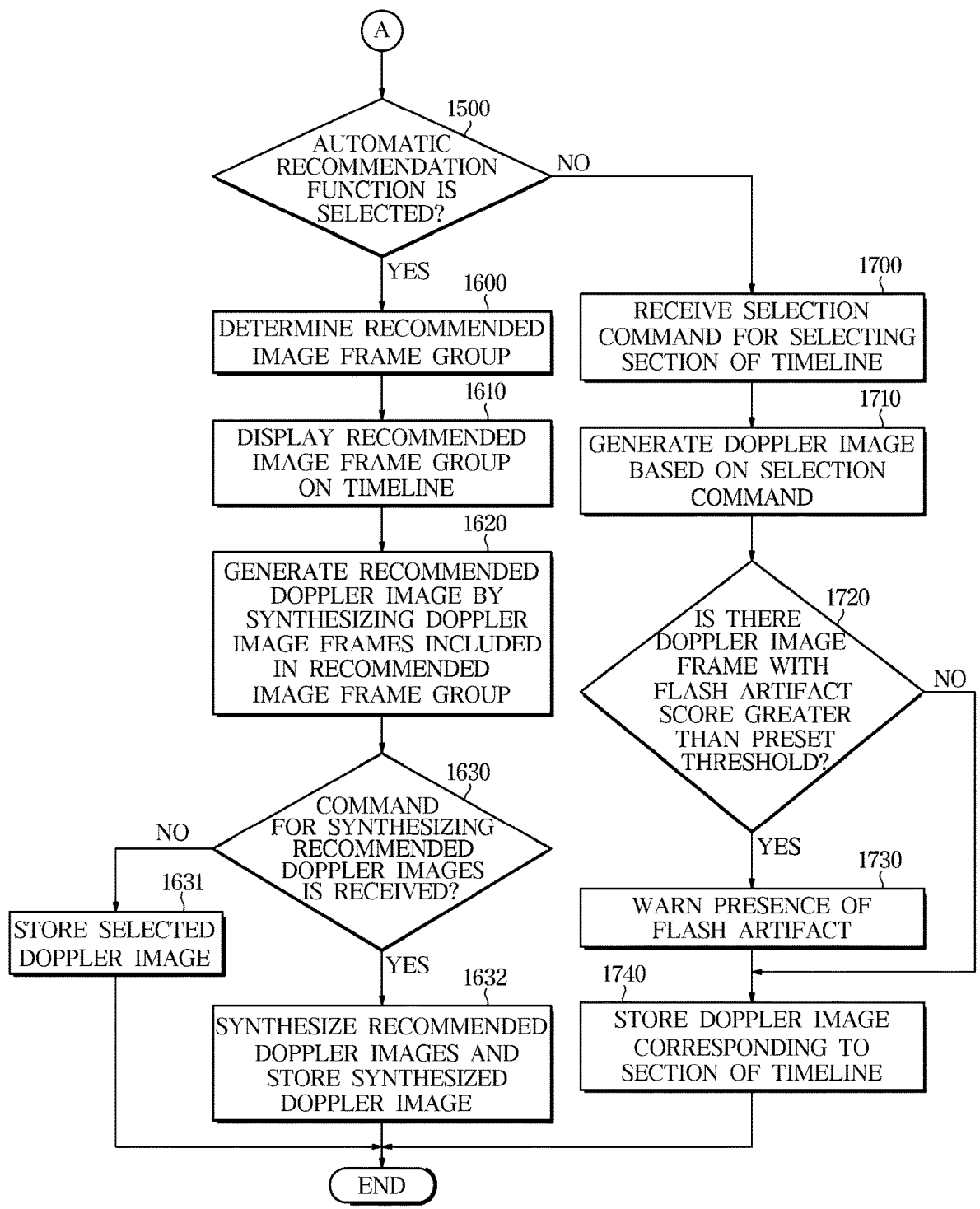

FIGS. 5 to 6 are control flowcharts of an ultrasound imaging apparatus according to an embodiment.

Referring to FIGS. 5 and 6 together, the probe P may irradiate ultrasound onto an object and receive an ultrasound echo signal reflected from the object (1000).

The image processor 140 may obtain a color Doppler signal from which the clutter signal has been removed by filtering the echo signal received from the probe P (1100).

Figure 7A:
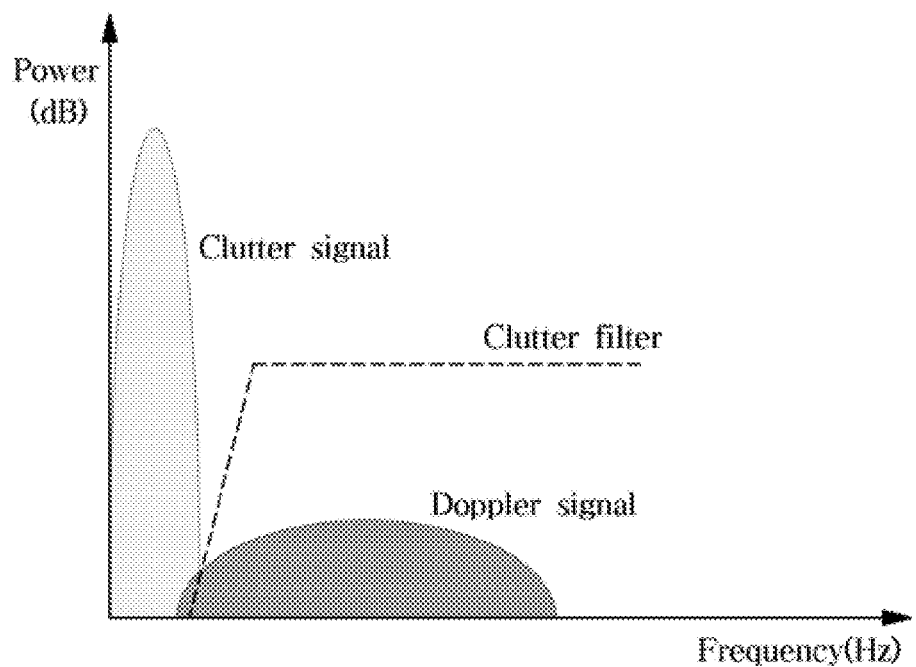
FIGS. 7A and 7B are diagrams illustrating a Doppler signal and a clutter signal present in an ultrasound echo signal.
Figure 7B:
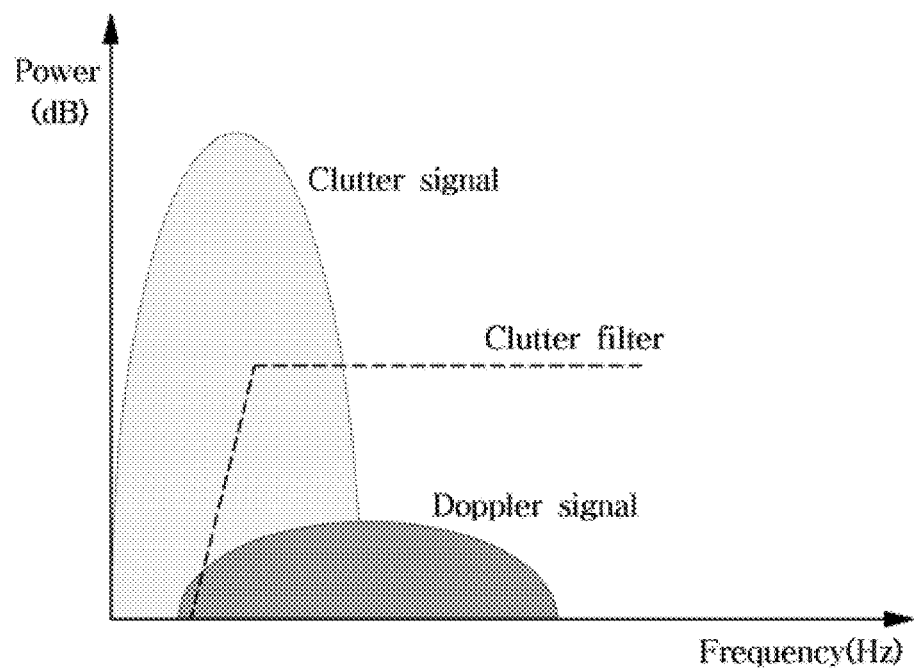

Specifically, referring to FIGS. 7A and 7B, the ultrasound echo signal may include a Doppler signal required for diagnosis and a clutter signal in a low frequency region unnecessary for diagnosis.

Such a clutter signal may be caused by various causes, for example, may be generated by the movement of the ultrasound probe P.

The image processor 140 may include a clutter filter capable of filtering a clutter signal in a low frequency region, and may filter an echo signal and obtain only a Doppler signal necessary for diagnosis. If the frequency band of the clutter signal does not overlap the frequency band of the Doppler signal, the image processor 140 may obtain a Doppler image without flash artifacts by obtaining only the Doppler signal through the clutter filter.

However, as shown in FIGS. 7A and 7B, when the frequency domain of the clutter signal is widened and overlaps with the frequency domain of the Doppler signal, the clutter signal cannot be completely removed even if a clutter filter is used.

In addition, even if the clutter signal is removed, a part of the Doppler signal is also removed, resulting in loss of blood flow signals.

Since the image processor 140 generates a Doppler image based on a plurality of Doppler image frames obtained by processing the echo signal, the Doppler image that the user may finally check is an image in which flash artifacts remain or an image generated by loss of blood flow signals.

Referring back to FIG. 5, the image processor 140 may generate a plurality of consecutive Doppler image frames based on a color Doppler signal from which a clutter signal has been completely or partially removed from an echo signal (1200).

The controller 150 may receive an ultrasound echo signal from the image processor 140 and calculate a flash artifact score of each of a plurality of Doppler image frames based on a clutter signal included in the ultrasound echo signal (1300).

Specifically, the controller 150 may calculate a flash artifact score based on the ultrasound echo signal, which is a signal before the image processor 140 filters the ultrasound echo signal and completely or partially removes the clutter signal.

The flash artifact score refers to the quantitative information of flash artifacts in a plurality of Doppler image frames.

The controller 150 may determine the flash artifact score of each of the plurality of Doppler image frames based on the power, speed, and standard deviation of the clutter signal included in the ultrasound echo signal.

Specifically, the flash artifact score may be calculated based on the following [Equation 1].

$$\text{flash artifact score} = \text{scailing}((\text{mean}(V_c)) + \text{std}(V_c)*2) \quad \text{[Equation 1]}$$

Here, $V_c$ means the speed of an ultrasound echo signal having a power greater than the average power of the ultrasound echo signal.

Thereafter, the controller 150 controls the image processor to generate a time line 161 corresponding to a plurality of Doppler image frames, and may control the display 160 to display flash artifact scores of each of the plurality of Doppler image frames on the timeline 161 (1400).

The timeline 161 may be generated in a bar shape corresponding to the acquisition order of a plurality of Doppler image frames, but the shape of the timeline 161 is not limited thereto.

In addition, any method of displaying the flash artifact score of each of the plurality of Doppler image frames on the timeline 161 may be used as long as the user may recognize the severity of the flash artifact score.

For example, the controller 150 may control the display 160 to directly display the flash artifact score on the timeline 161, and may indicate the severity of the flash artifact score in color or as a pattern.

Figure 8:
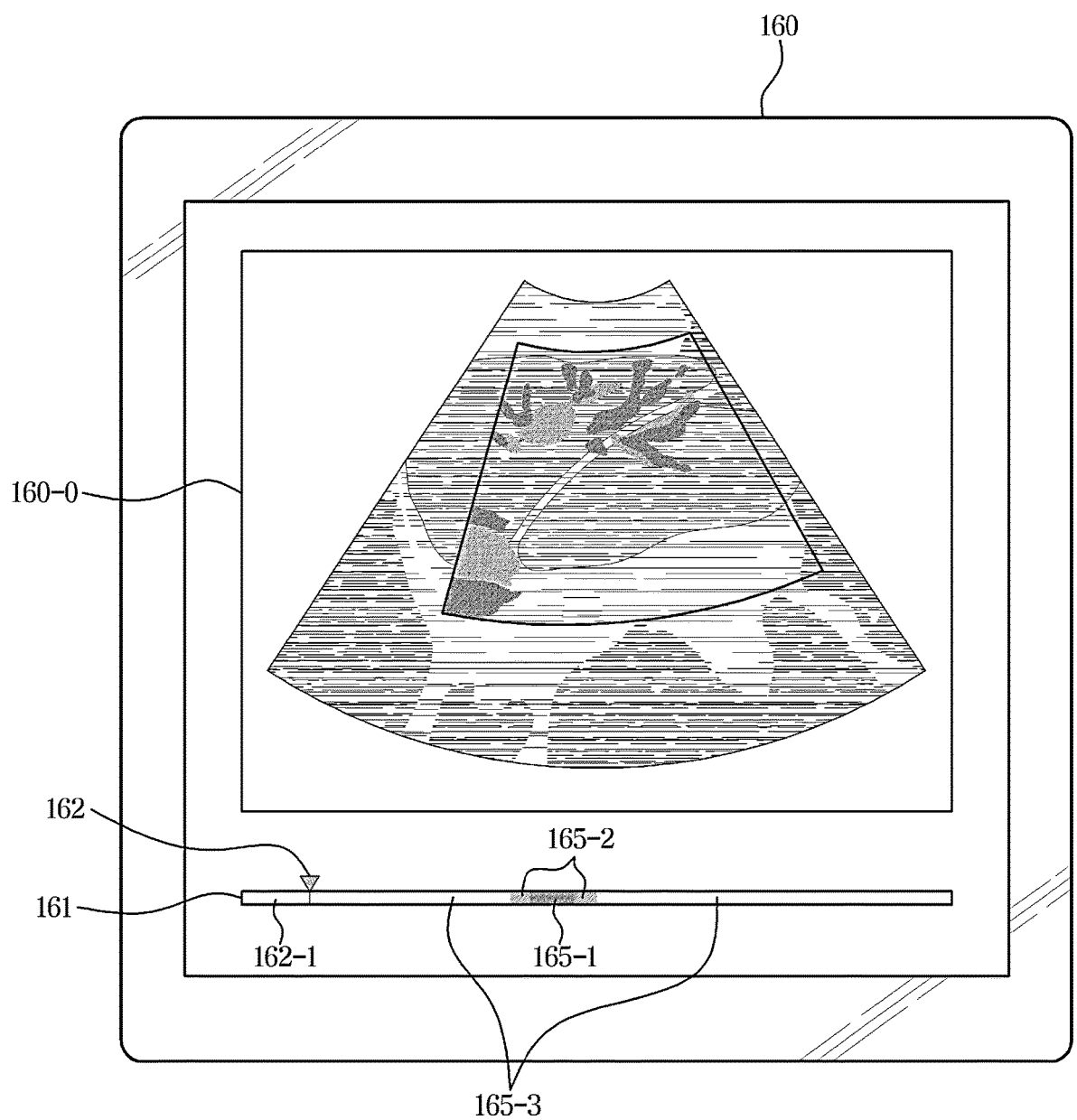
FIG. 8 is a diagram illustrating a color Doppler image and a timeline displayed on an ultrasound imaging apparatus according to an embodiment.

Referring to FIG. 8, the display 160 may display a Doppler image 160-0 generated by the image processor 140 based on a control signal from the controller 150 and may display a bar-shaped timeline 161 corresponding to a plurality of Doppler image frames included in the Doppler image 160-0.

The controller 150 according to an embodiment may indicate a flash artifact score of each of a plurality of Doppler image frames by displaying colors on the timeline 161.

For example, as shown in FIG. 8, the controller 150 may display the color of the first section 165-1 corresponding to Doppler image frames having a flash artifact score higher than the first threshold on the timeline 161 in a dark color.

In addition, the controller 150 may display the color of the second section 165-2 corresponding to the Doppler image frames having a flash artifact score smaller than the first threshold but higher than the second threshold on the timeline 161 to be lighter than the first section 165-1.

In addition, the controller 150 may display the color of the third section 165-3 corresponding to the Doppler image frames having a flash artifact score smaller than the second threshold on the timeline 161 to be lighter than the second section 165-2.

The controller 150 may display the first section 165-1 in red, the second section 165-2 in orange, and the third section 165-3 in blue on the timeline 161.

At this time. The first and second thresholds, which are thresholds for comparing the severity of flash artifacts, may be determined by initial setting, and the above threshold value may include a plurality of values to display the severity of the flash artifact score in more detail.

Although not shown in FIG. 5, the controller 150 may determine whether the probe P is scanning the object based on the difference between the ultrasound echo signal and the color Doppler signal, and may generate the timeline 161 by displaying a time point at which the probe P starts scanning the object on the timeline 161.

Specifically, when the difference between the average power of the ultrasound echo signal and the average power of the color Doppler signal is greater than the preset power, or when the difference between the average power of the ultrasound echo signal and the average power of the color Doppler signal is less than the first power and the difference between the average speed of the ultrasound echo signal and the average speed of the color Doppler signal is less than a preset speed, the controller 150 may determine that the probe P is scanning the object.

Referring to FIG. 8, the controller 150 displays the marker 162 on the timeline 161 to indicate the scan start time of the probe P.

However, the method of displaying the scan start point of the probe P is not limited thereto, and it may be variously changed by a person skilled in the art.

As described above, the ultrasound imaging apparatus 100 according to an embodiment may induce a user not to check unnecessary data 162-1 before the scan starts by displaying the scan start point of the probe P.

Referring to FIG. 6, an input 170 may receive a selection command for an automatic recommendation function from a user (1500).

The automatic recommendation function may mean a function of recommending a set of Doppler image frames that are meaningful for diagnosis among a plurality of Doppler image frames obtained by the image processor 140 or an image synthesized from the set to a user.

Figure 9:
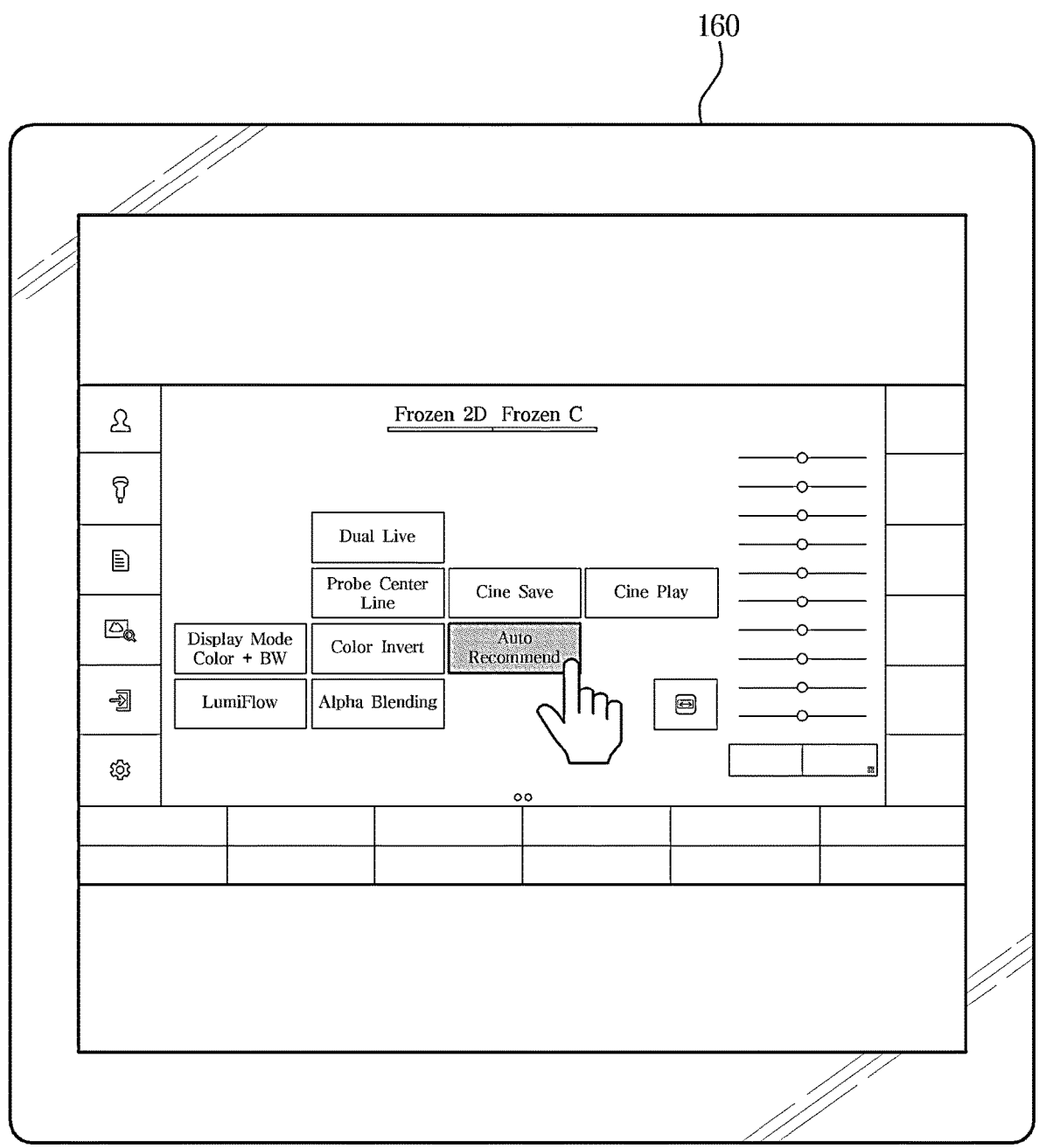
FIG. 9 is a diagram illustrating an example in which an ultrasound imaging apparatus according to an embodiment receives an automatic recommendation function.

As shown in FIG. 9, the controller 150 controls the display 160 to display a user interface (UI) through which selection command for an automatic recommendation function may be input, and the user may input the selection command for the automatic recommendation function through the input 170.

When the automatic recommendation function is selected through input 170 (YES in 1500), the controller 150 may determine a set of Doppler image frames having a flash artifact score equal to or less than a preset threshold among a plurality of Doppler image frames acquired from the image processor 140 and being continuous with each other as a recommended image frame group (1600).

In this case, the preset threshold may be set in advance by the user or the designer of the ultrasound imaging apparatus 100, and for example, may be set smaller than the second threshold described above.

In addition, the preset threshold may be automatically set using a statistical result of a flash artifact score, and may include one or more threshold values.

For convenience of explanation, it is assumed that there are a first Doppler image frame, a second Doppler image frame, a third Doppler image frame, a fourth Doppler image frame, and a fifth Doppler image frame obtained in the order described, and it is assumed that the first Doppler image frame, the second Doppler image frame, the fourth Doppler image frame, and the fifth Doppler image frame have a flash artifact score less than or equal to the preset threshold, and that only the third Doppler image frame has a flash artifact score greater than or equal to the preset threshold.

In this case, the flash artifact score is less than or equal to the preset threshold and the first Doppler image frame and the second Doppler image frame that are continuous with each other may be determined as one recommended image frame group, similarly, the fourth Doppler image frame and the fifth Doppler image frame may also be determined as another recommended image frame group. However, since the flash artifact score of the third Doppler image frame is larger than the preset threshold, the second Doppler image frame and the fourth Doppler image frame, which are not continuous with each other, cannot be determined as one recommended image frame group.

In other words, there may be a plurality of recommended image frame groups.

The controller 150 may control the display 160 so that a section corresponding to the recommended image frame group is displayed on the timeline 161 to be distinguished from a section not corresponding to the recommended image frame group (1610).

Figure 10:
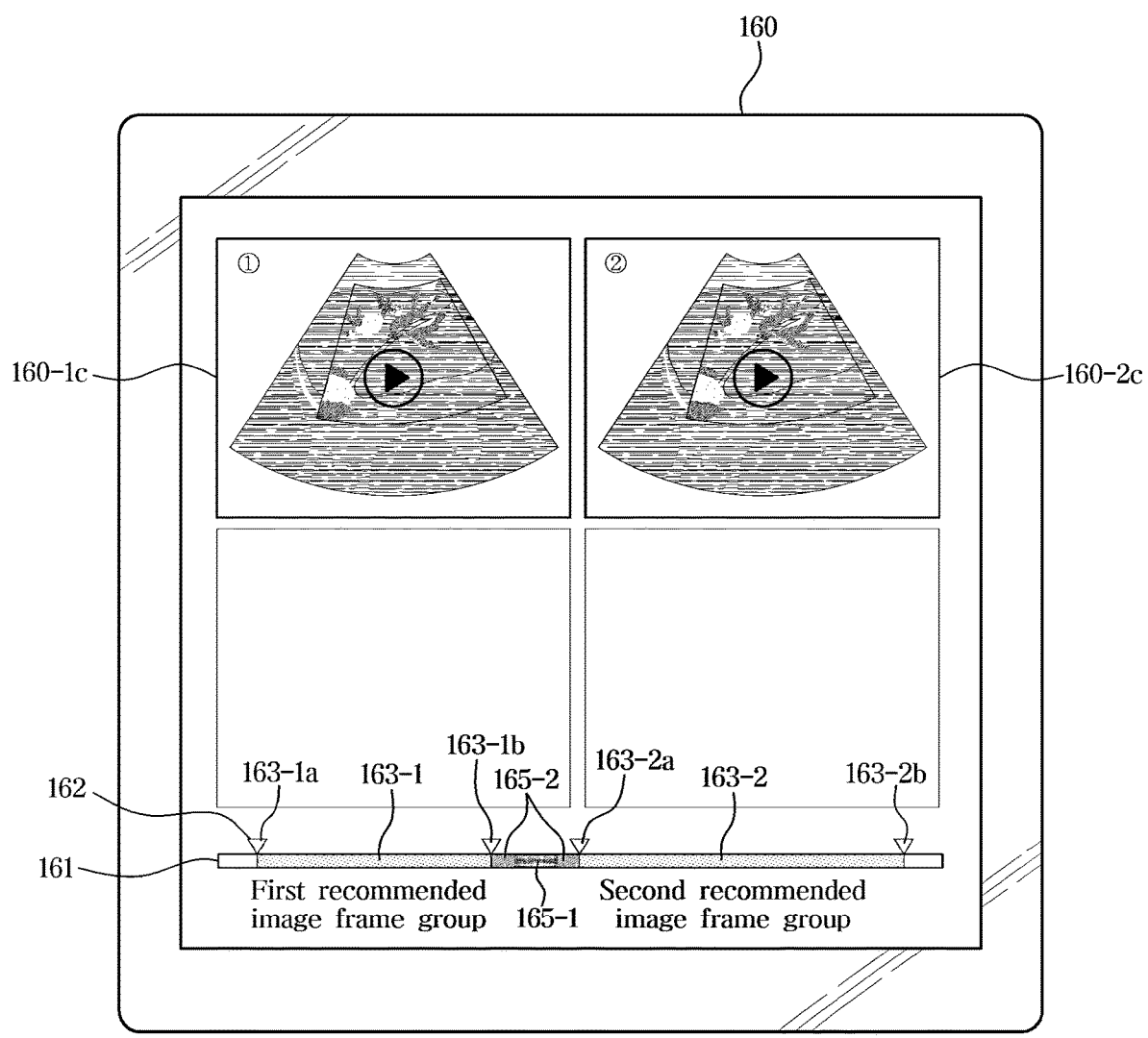
FIG. 10 is a diagram illustrating a process of generating a recommended Doppler image by an ultrasound imaging apparatus according to an embodiment.

For example, referring to FIG. 10, the controller 150 may display a recommended image frame group by controlling the display 160 to display markers on the timelines 163-1*a* and 163-2*a* corresponding to the Doppler image frame obtained first among Doppler image frames 163-1 and 163-2 included in the recommended image frame group and on the timelines 163-1*b* and 163-2*b* corresponding to the last obtained Doppler image frame.

As described above, the controller 150 may control the display 160 so that the color or pattern of the timelines corresponding to Doppler image frames 163-1 and 163-2 included in the recommended image frame group and timelines 165-1 and 165-2 corresponding to Doppler image frames not included in the recommended image frame group are displayed differently.

For example, the controller 150 may display the color of the timeline corresponding to the Doppler image frames 163-1 included in the first recommended image frame group and the color of the timeline 161 corresponding to the Doppler image frames 163-2 included in the second recommended image frame group in green. In addition, as described above, the controller 150 may display the color of the timeline 161 that does not correspond to the recommended image frame group in red or orange depending on the severity of the flash artifact score.

Further, the controller 150 may control the image processor 140 to synthesize Doppler image frames included in the recommended image frame group, and the image processor 140 may generate a recommended Doppler image by synthesizing Doppler image frames included in the recommended image frame group (1620).

Referring to FIG. 10, the image processor 140 may generate a first Doppler image 163-1*c* by synthesizing Doppler image frames 163-1 included in the first recommended image frame group and may generate a second Doppler image 163-2*c* by synthesizing the Doppler image frames 163-2 included in the second recommended image frame group.

The controller 150 may control the display 160 to display the first Doppler image 163-1*c* and the second Doppler image 163-2*c* generated by the image processor 140, respectively.

The input 170 may receive a synthesis command for synthesizing recommended Doppler images (the first Doppler image 163-1*c* and the second Doppler image 163-2*c*) from the user (1630).

When the synthesis command is not received from the input 170 (No in 1630) and the selection command of the recommended Doppler image is received, the controller 150 may store the selected Doppler image in the storage 180 (1631). For example, in FIG. 10, when the user selects the first Doppler image 163-1*c* from among the first Doppler image 163-1*c* and the second Doppler image 163-2*c* displayed on the display 160, the controller 150 may store the first Doppler image 163-1c in the storage 180.

When receiving a synthesis command from the input 170 (YES in 1630), the controller 150 synthesizes the recommended Doppler images 163-1c and 163-2c by controlling the image processor 140 to generate one Doppler image and may store the synthesized Doppler image in the storage 180 (1632).

In addition, the controller 150 may control the display 160 to display the synthesized Doppler image.

Figure 11:
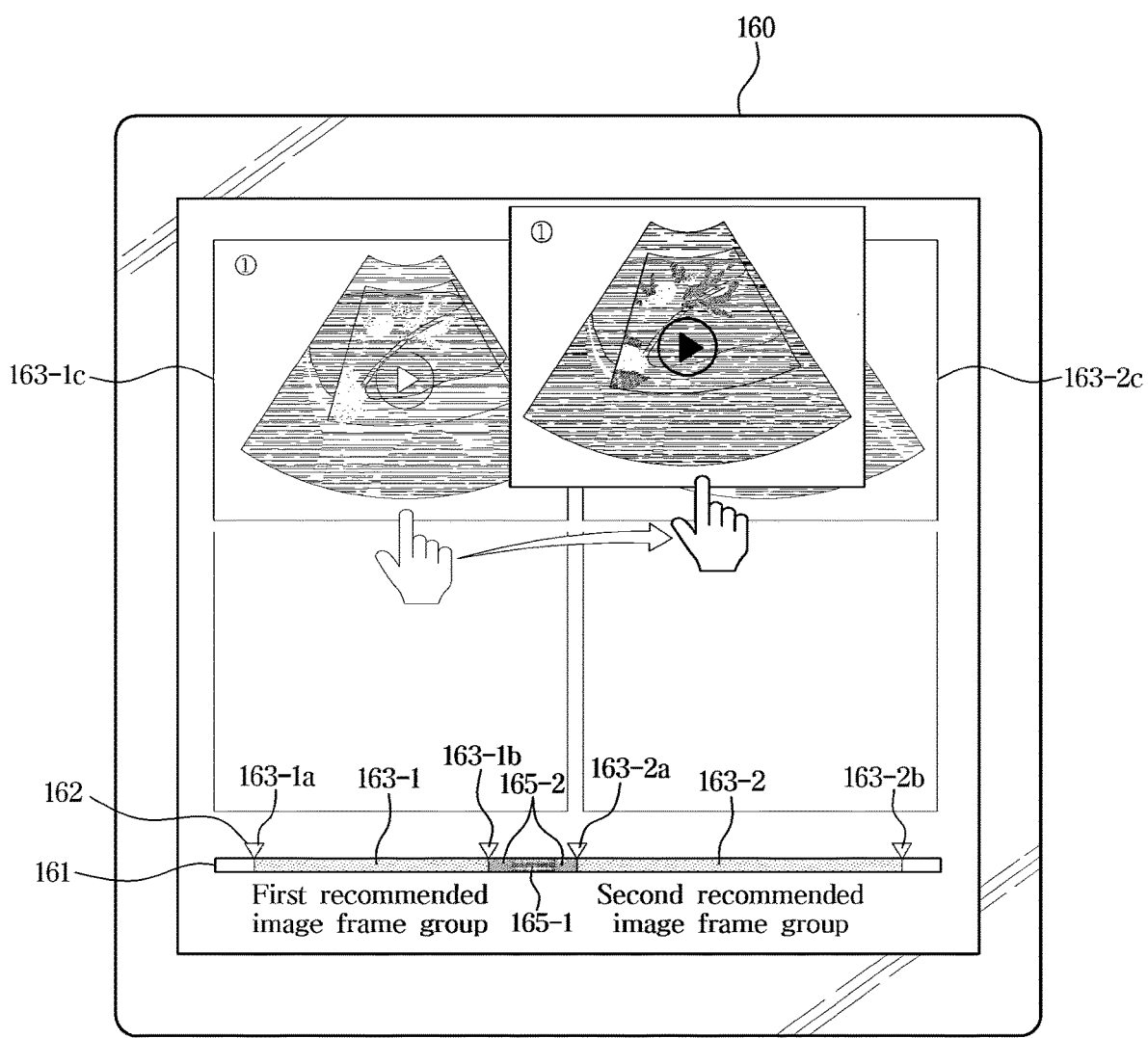
FIG. 11 is a diagram illustrating an example in which an ultrasound imaging apparatus according to an embodiment receives a command for synthesizing a recommended Doppler image.

Referring to FIG. 11, as an example of the synthesis command, the user drags the first Doppler image 163-1c displayed on the display 160 and places it on the second Doppler image 163-2c, or may input a synthesis command by dragging the second Doppler image 163-2c displayed on the display 160 and placing it on the first Doppler image 163-1c.

When the input 170 includes a mouse, the user may manipulate the mouse to move the cursor displayed on the display 160, and may click the mouse while placing the cursor on the first Doppler image 163-1c and drag it on the second Doppler image 163-2c.

When the input 170 includes a touch panel, the user may directly touch the first Doppler image 163-1c displayed on the display 160 and then drag it onto the second Doppler image 163-2c.

As described above, the ultrasound imaging apparatus 100 according to an embodiment generates a plurality of images meaningful for diagnosis and displays them on the display 160, so that the user may easily synthesize images that are meaningful for diagnosis.

Referring back to FIG. 6, the input 170 may receive a selection command for selecting a section of the timeline 161, and the controller 150 may receive a selection command from the input 170 (1700).

In the drawing, when the automatic recommendation function is not selected, it is shown that a selection command for selecting a section of the timeline 161 is received. However, even if the automatic recommendation function is selected, the user may select a section of the timeline 161 through the input 170.

Figure 12:
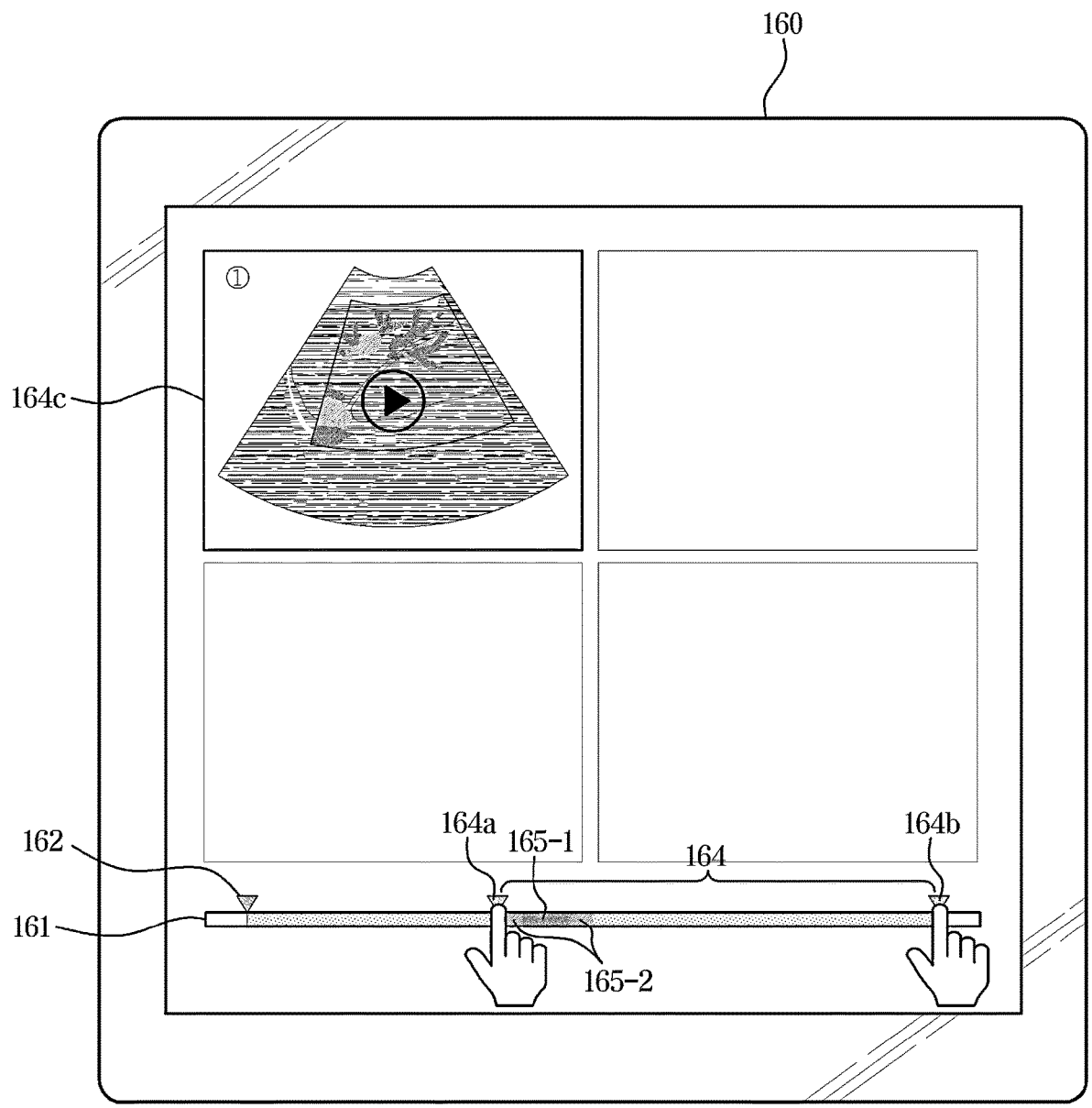
FIG. 12 is a diagram illustrating an example in which an ultrasound imaging apparatus according to an embodiment receives a command for selecting a section of a timeline.

Referring to FIG. 12, the controller 150 may control the image processor 140 to synthesize Doppler image frames corresponding to the section 164 of the selected timeline based on the selection command, and the image processor 140 may generate a Doppler image 164-1 by synthesizing Doppler image frames corresponding to the section 164 of the selected timeline based on the selection command (1710).

By selecting two points 164a and 164b of the timeline 161 displayed on the display 160, the user may select a section 164 of the timeline corresponding therebetween.

For example, when the input 170 includes a mouse, the user manipulates the mouse to position the cursor displayed on the display 160 at any one position 164a on the timeline 161 and then may select a section of the timeline 161 by dragging the cursor to the desired position 164b.

When there is a Doppler image frame with a flash artifact score greater than the preset threshold among the Doppler image frames corresponding to the section 164 of the selected timeline (YES in 1720), the controller 150 may control the display 160 to display a warning image warning of the presence of flash artifacts in the synthesized Doppler image (1730).

Figure 13:
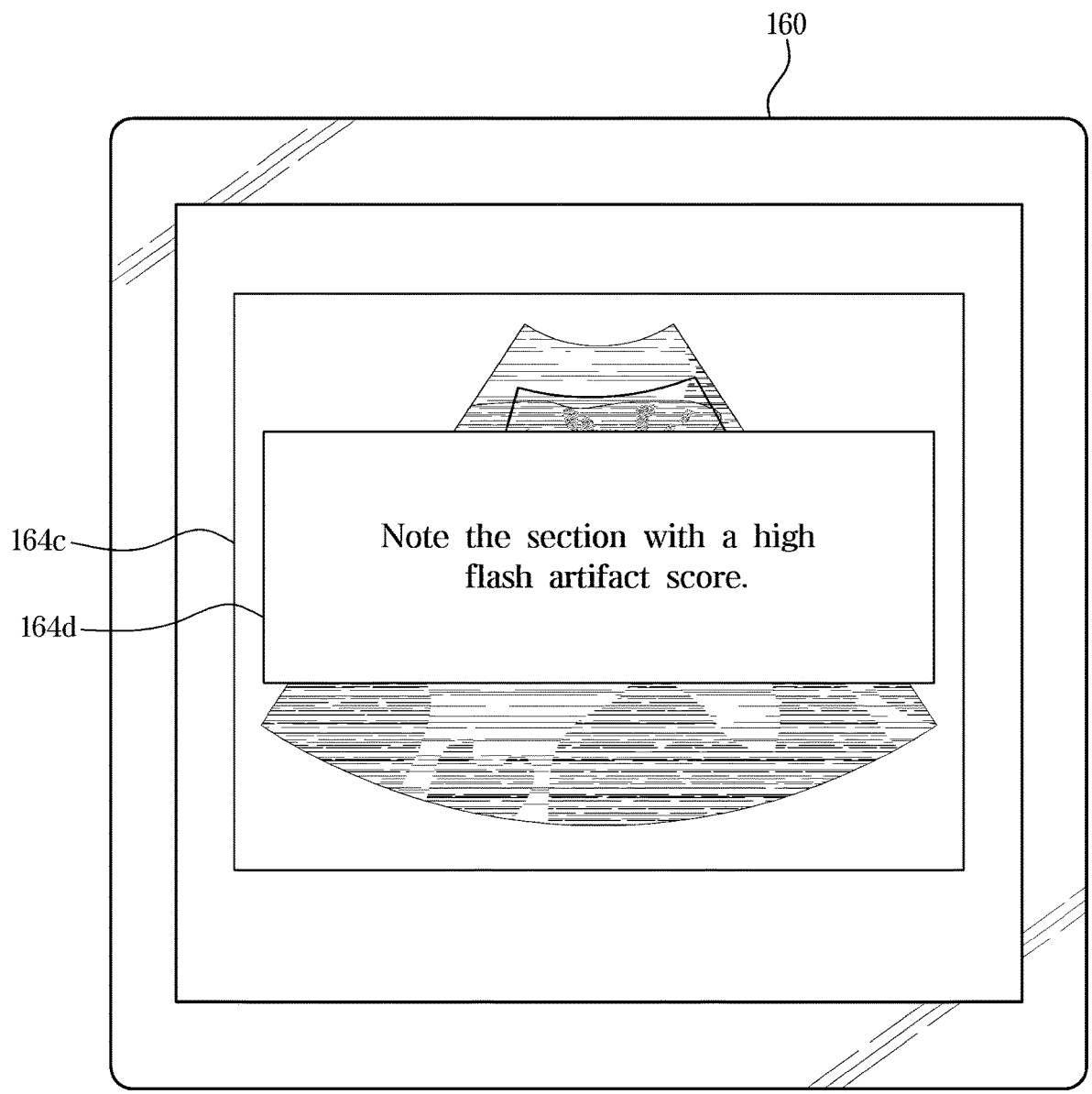
FIG. 13 is a diagram illustrating an example in which an ultrasound imaging apparatus according to an embodiment displays a warning image.

In the case of the situation shown in FIG. 12, Doppler image frames included in the first section 165-1 and the second section 165-2 on the timeline 161 are Doppler image frames with a flash artifact score greater than a preset threshold, and a part of the first section 165-1 and the second section 165-2 is included in the user's selection section 164. Accordingly, the controller 150 may control the display 160 to display a warning image 164d that warns of the presence of flash artifacts, as shown in FIG. 13.

The controller 150 may control the image processor 140 to synthesize Doppler image frames included in the selected section 164 and generate a third Doppler image 164c.

The controller 150 may control the display 160 to display a third Doppler image 164c, and when receiving the selection command of the third Doppler image 164c from the user through the input 170, the controller 150 may store the selected third Doppler image 164c in the storage 180 (1740).

According to the above-described ultrasound imaging apparatus 100 and control method thereof, it is possible to induce the user to store an image section that is meaningful for diagnosis by notifying a user of an image section in which there are few flash artifacts in a color Doppler image.

In addition, by automatically suggesting an image section with few flash artifacts to the user, the user may easily obtain an image meaningful for diagnosis.

In addition, when there are a plurality of recommended images, the user's request may be reflected by allowing the recommended images to be synthesized according to the user's selection.

Meanwhile, the disclosed embodiments may be implemented in the form of a recording medium storing instructions that are executable by a computer. The instructions may be stored in the form of a program code, and when executed by a processor, the instructions may generate a program module to perform operations of the disclosed embodiments. The recording medium may be implemented as a computer-readable recording medium.

The computer-readable recording medium may include all kinds of recording media storing commands that may be interpreted by a computer. For example, the computer-readable recording medium may be ROM, RAM, a magnetic tape, a magnetic disc, flash memory, an optical data storage device, etc.

In addition, the computer-readable recording medium may be provided in the form of a non-transitory storage medium. Here, 'non-transitory storage medium' is a tangible device and only means that it does not contain a signal (e.g., electromagnetic wave). This term does not distinguish between a case where data is stored semi-permanently in a storage medium and a case that is temporarily stored. For example, the 'non-transitory storage medium' may include a buffer in which data is temporarily stored.

According to an embodiment, a method according to various embodiments disclosed in the present document may be provided by being included in a computer program product. Computer program products may be traded between sellers and buyers as commodities. Computer program products are distributed in the form of a device-readable recording medium (e.g. compact disc read only memory (CD-ROM)), or may be distributed (eg, downloaded or uploaded) through an application store (eg, Play Store™) or directly or online between two user devices (eg, smartphones). In the case of online distribution, at least a portion of the computer program product (e.g., downloadable app) is at least temporarily stored in a device-readable recording medium such as the manufacturers server, the application store's server, or the relay server's memory, or may temporarily be generated.

The exemplary embodiments of the disclosure have thus far been described with reference to the accompanying drawings. It will be obvious to those of ordinary skill in the art that the disclosure may be practiced in other forms than the exemplary embodiments as described above without changing the technical idea or essential features of the disclosure. The above exemplary embodiments are only by way of example, and should not be interpreted in a limited sense.

According to an ultrasound imaging apparatus and a control method thereof according to an aspect, a user can easily select a section meaningful for diagnosis within a color Doppler image.

What is claimed is:

1. An ultrasound imaging apparatus comprising:
a probe configured to irradiate an ultrasound signal to an object and receive an ultrasound echo signal reflected from the object;
an image processor configured to obtain a color Doppler signal from which a clutter signal has been completely or partially removed by filtering the ultrasound echo signal, obtain a plurality of consecutive Doppler image frames based on the color Doppler signal and generate a Doppler image based on the plurality of consecutive Doppler image frames;
a display configured to output the Doppler image; and
a controller configured to calculate a flash artifact score of each of the plurality of consecutive Doppler image frames based on the ultrasound echo signal, generate a timeline corresponding to the plurality of consecutive Doppler image frames and control the display so that the flash artifact score of each of the plurality of consecutive Doppler image frames appear on the timeline,
wherein the controller is configured to determine whether the probe is scanning the object and control the display to display an indicator representing a time point at which the probe starts to scan the object on the timeline.

2. The ultrasound imaging apparatus of claim 1, wherein the controller is configured to determine a set of Doppler image frames whose flash artifact score is less than or equal to a preset threshold and which are continuous with each other, among the plurality of consecutive Doppler image frames as a recommended image frame group and control the display so that a section corresponding to the recommended image frame group is displayed on the timeline to be distinguished from a section not corresponding to the recommended image frame group.

3. The ultrasound imaging apparatus of claim 2, wherein the image processor is configured to generate a recommended Doppler image by synthesizing Doppler image frames comprised in the recommended image frame group.

4. The ultrasound imaging apparatus of claim 2, wherein the controller is configured to control the display so that a marker is displayed on a timeline corresponding to the earliest obtained Doppler image frame and the latest obtained Doppler image frame among Doppler image frames comprised in the recommended image frame group.

5. The ultrasound imaging apparatus of claim 2, wherein the controller is configured to control the display so that a color or pattern of a timeline corresponding to Doppler image frames comprised in the recommended image frame group and a timeline corresponding to Doppler image frames not comprised in the recommended image frame group are displayed differently.

6. The ultrasound imaging apparatus of claim 2, wherein the recommended image frame group comprises a first recommended image frame group and a second recommended image frame group,
wherein the image processor is configured to generate a first Doppler image from which Doppler image frames comprised in the first recommended image frame group are synthesized and a second Doppler image from which Doppler image frames comprised in the second recommended image frame group are synthesized, respectively, and
wherein the controller is configured to control the display to display the first Doppler image and the second Doppler image, respectively.

7. The ultrasound imaging apparatus of claim 6, further comprising:
an input configured to receive a synthesis command for synthesizing the first Doppler image and the second Doppler image from a user, and
wherein the image processor is configured to generate one Doppler image by synthesizing the first Doppler image and the second Doppler image when receiving the synthesis command.

8. The ultrasound imaging apparatus of claim 1, wherein the flash artifact score is quantitative information of flash artifact in the plurality of Doppler image frames, and
wherein the controller is configured to determine the flash artifact score of each of the plurality of Doppler image frames based on the power, speed and standard deviation of the ultrasound echo signal.

9. The ultrasound imaging apparatus of claim 1, wherein the controller is configured to determine whether the probe is scanning the object based on a difference between the ultrasound echo signal and the color Doppler signal.

10. A control method of an ultrasound imaging apparatus, the method comprising:
irradiating an ultrasound signal to an object and receiving an ultrasound echo signal reflected from the object;
obtaining a color Doppler signal from which a clutter signal has been completely or partially removed by filtering the ultrasound echo signal;
obtaining a plurality of consecutive Doppler image frames based on the color Doppler signal;
generating a Doppler image based on the plurality of consecutive Doppler image frames;
outputting the Doppler image;
calculating a flash artifact score of each of the plurality of consecutive Doppler image frames based on the ultrasound echo signal;
generating a timeline corresponding to the plurality of consecutive Doppler image frames;
displaying the flash artifact score of each of the plurality of consecutive Doppler image frames on the timeline;
determining whether the ultrasound imaging apparatus is scanning the object; and
displaying an indicator representing a time point at which the ultrasound imaging apparatus starts to scan the object on the timeline.

11. The control method of claim 10, further comprising:
determining a set of Doppler image frames whose flash artifact score is less than or equal to a preset threshold and which are continuous with each other, among the plurality of consecutive Doppler image frames as a recommended image frame group; and displaying a section corresponding to the recommended image frame group on the timeline to be distinguished from a section not corresponding to the recommended image frame group.

12. The control method of claim 11, further comprising:
generating a recommended Doppler image by synthesizing Doppler image frames comprised in the recommended image frame group.

13. The control method of claim 11, wherein the displaying a section corresponding to the recommended image frame group on the timeline to be distinguished from a section not corresponding to the recommended image frame group comprises:
displaying a marker on a timeline corresponding to the earliest obtained Doppler image frame and the latest obtained Doppler image frame among Doppler image frames comprised in the recommended image frame group.

14. The control method of claim 11, wherein the displaying a section corresponding to the recommended image frame group on the timeline to be distinguished from a section not corresponding to the recommended image frame group comprises:
displaying a color or pattern of a timeline corresponding to Doppler image frames comprised in the recommended image frame group and a timeline corresponding to Doppler image frames not comprised in the recommended image frame group, differently.

15. The control method of claim 11, wherein the recommended image frame group comprises a first recommended image frame group and a second recommended image frame group, and
wherein the control method further comprises:
generating a first Doppler image from which Doppler image frames comprised in the first recommended image frame group are synthesized and a second Doppler image from which Doppler image frames comprised in the second recommended image frame group are synthesized, respectively; and
displaying the first Doppler image and the second Doppler image, respectively.

16. The control method of claim 15, further comprising:
receiving a synthesis command for synthesizing the first Doppler image and the second Doppler image from a user; and
generating one Doppler image by synthesizing the first Doppler image and the second Doppler image when receiving the synthesis command.

17. The control method of claim 16, further comprising:
receiving a selection command for selecting a section of the timeline;
generating a Doppler image by synthesizing Doppler image frames corresponding to the section of the selected timeline based on the selection command; and displaying a warning image warning of the presence of flash artifact in the Doppler image by controlling the display when there is a Doppler image frame with the flash artifact score greater than the preset threshold among the Doppler image frames corresponding to the section of the selected timeline.

18. The control method of claim 10, wherein the flash artifact score is quantitative information of flash artifact in the plurality of Doppler image frames, and
wherein the calculating a flash artifact score of each of the plurality of Doppler image frames based on the ultrasound echo signal comprises:
determining the flash artifact score of each of the plurality of Doppler image frames based on the power, speed and standard deviation of the ultrasound echo signal.

19. The control method of claim 10, wherein the determining whether the ultrasound imaging apparatus is scanning the object comprises:
determining whether the ultrasound imaging apparatus is scanning the object based on the difference between the ultrasound echo signal and the color Doppler signal.

20. An ultrasound imaging apparatus comprising:
a probe configured to irradiate an ultrasound signal to an object and receive an ultrasound echo signal reflected from the object;
an image processor configured to obtain a color Doppler signal from which a clutter signal has been completely or partially removed by filtering the ultrasound echo signal, obtain a plurality of consecutive Doppler image frames based on the color Doppler signal and generate a Doppler image based on the plurality of consecutive Doppler image frames;
a display configured to output the Doppler image;
a controller configured to calculate a flash artifact score of each of the plurality of consecutive Doppler image frames based on the ultrasound echo signal, generate a timeline corresponding to the plurality of consecutive Doppler image frames and control the display so that the flash artifact score of each of the plurality of consecutive Doppler image frames appear on the timeline; and
an input configured to receive a selection command for selecting a section of the timeline,
wherein the image processor is configured to generate the Doppler image by synthesizing Doppler image frames corresponding to the section of the selected timeline based on the selection command, and
wherein the controller is configured to control the display to display a warning image warning of the presence of flash artifact in the Doppler image when there is a Doppler image frame with the flash artifact score greater than a preset threshold among the Doppler image frames corresponding to the section of the selected timeline.

* * * * *